(12) United States Patent
Briggs

(10) Patent No.: US 12,076,362 B2
(45) Date of Patent: Sep. 3, 2024

(54) BOTANICAL PAIN RELIEF OINTMENT

(71) Applicant: Mildred Brenda Briggs, Dallas, GA (US)

(72) Inventor: Mildred Brenda Briggs, Dallas, GA (US)

( * ) Notice: Subject to any disclaimer, the term of this patent is extended or adjusted under 35 U.S.C. 154(b) by 0 days.

(21) Appl. No.: 17/659,507

(22) Filed: Apr. 18, 2022

(65) Prior Publication Data

US 2023/0330175 A1  Oct. 19, 2023

(51) Int. Cl.
| | | |
|---|---|---|
| *A61K 31/05* | (2006.01) |
| *A61K 36/324* | (2006.01) |
| *A61K 36/328* | (2006.01) |
| *A61K 36/534* | (2006.01) |
| *A61K 36/63* | (2006.01) |
| *A61K 36/90* | (2006.01) |
| *A61K 36/9066* | (2006.01) |
| *A61K 47/44* | (2017.01) |

(52) U.S. Cl.
CPC .......... *A61K 36/9066* (2013.01); *A61K 31/05* (2013.01); *A61K 36/324* (2013.01); *A61K 36/328* (2013.01); *A61K 36/534* (2013.01); *A61K 36/63* (2013.01); *A61K 47/44* (2013.01)

(58) Field of Classification Search
None
See application file for complete search history.

(56) References Cited

PUBLICATIONS

Wayback machine entry for Lily Hill, accessed online Jul. 14, 2023. (Year: 2023).*
Wayback machine entry for Gabriel's Light, accessed online Jul. 14, 2023. (Year: 2023).*
Lily Hill (CBD Salve, Original Strength, available online Oct. 30, 2020) (Year: 2020).*
Gabriel's Light (Frankincense, Gold, and Myrrh Essential Oil Blend, available online Sep. 29, 2020) (Year: 2020).*

* cited by examiner

*Primary Examiner* — Melissa S Mercier
(74) *Attorney, Agent, or Firm* — Dunlap Bennett & Ludwig, PLLC; Anna L. Kinney

(57) ABSTRACT

A botanical pain relief ointment contains a botanical fat base, turmeric oil, myrrh oil, frankincense oil, peppermint oil, an anti-inflammatory botanical oil, and CBD isolate oil. A method of producing the botanical pain relief ointment includes sequentially mixing shea butter, turmeric oil, myrrh oil, frankincense oil, peppermint oil, olive oil, and CBD isolate oil in a blender on low speed until creamy and smooth. The ointment is all natural and is believed to have no side effects.

3 Claims, 1 Drawing Sheet

BOTANICAL PAIN RELIEF OINTMENT

BACKGROUND OF THE INVENTION

The present invention relates to topical pain relief and, more particularly, to a botanical pain relief ointment.

It is difficult to find an effective all-natural topical product to relieve minor aches and pains.

As can be seen, there is a need for an effective all-natural topical pain reliever.

SUMMARY OF THE INVENTION

In one aspect of the present invention, a botanical pain relief ointment is provided, comprising: a botanical fat base, turmeric oil, myrrh oil, frankincense oil, peppermint oil, an anti-inflammatory botanical oil, and cannabidiol (CBD) isolate oil.

In another aspect of the present invention, a method of producing a botanical pain relief ointment is provided, comprising sequentially mixing shea butter, turmeric oil, myrrh oil, frankincense oil, peppermint oil, olive oil, and CBD isolate oil in a blender on low speed until creamy and smooth.

These and other features, aspects and advantages of the present invention will become better understood with reference to the following drawings, description, and claims.

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a pain relief ointment comprising several botanicals oils in a botanical butter base. The composition is all natural and is believed to have no side effects. It may be made from organic ingredients.

The inventive composition may include a base for components, such as shea butter.

The inventive composition may include turmeric oil, which is believed to promote healthy circulation.

The inventive composition may include myrrh oil, which is believed to combat pain and swelling.

The inventive composition may include frankincense oil, which is believed to relieve stress.

The inventive composition may include peppermint oil, which is believed to improve circulation and skin health in general.

The composition may include an anti-inflammatory agent such as olive oil.

The composition may include CBD isolate oil, which is believed to relieve pain and anxiety.

To produce the inventive composition, all the components may be mixed using a blender on low speed for about 10-15 minutes or until creamy and smooth. Preferably, the components are added to the blender in the following sequence: shea butter, turmeric oil, myrrh oil, frankincense oil, peppermint oil, olive oil, and CBD isolate oil.

The composition may be applied topically to relieve pain. To use the pain relief butter, the user may apply the composition to an affected area and massage the area in a circular motion.

Figure 1:
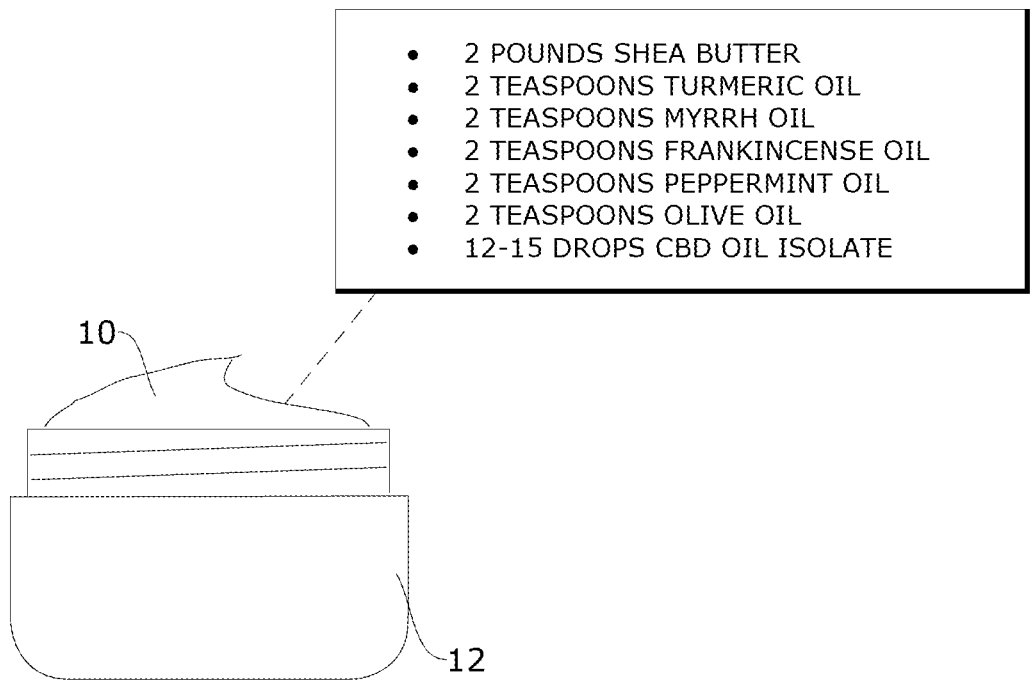
FIG. 1 is a side elevation view of a container containing a composition according to an embodiment of the present invention.
Figure 2:
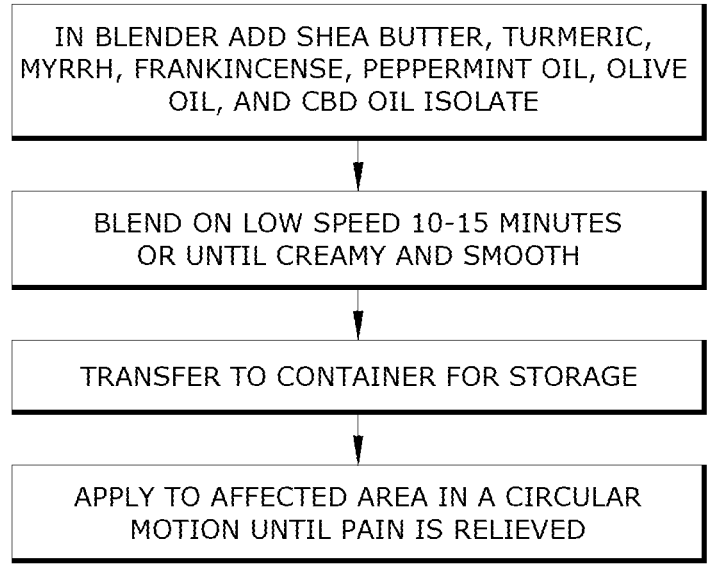
FIG. 2 is a flow chart of a process of making and using the composition of FIG. 1.

Referring to FIGS. 1 and 2, a container 12 containing an exemplary pain relief composition according to an embodiment of the present invention is shown in FIG. 1. In this example, the pain relief composition comprises about 2 pounds of shea butter; about 2 teaspoons each of turmeric oil, myrrh oil, frankincense oil, peppermint oil, and olive oil; and about 12 drops of CBD oil isolate, containing about 25 mg CBD isolate per 0.5 mL. In other words, the composition is predominantly a botanical fat base and the essential oils may be provided in about equal amounts. FIG. 2 illustrates steps of manufacturing and using the inventive composition.

It should be understood, of course, that the foregoing relates to exemplary embodiments of the invention and that modifications may be made without departing from the spirit and scope of the invention as set forth in the following claims.

What is claimed is:

1. A botanical pain relief ointment of consisting of shea butter, turmeric oil, myrrh oil, frankincense oil, peppermint oil, olive oil, and CBD isolate oil.

2. The botanical pain relief ointment of claim 1, wherein the botanical pain relief ointment contains equal percentages by volume of the turmeric oil, myrrh oil, frankincense oil, peppermint oil, and the olive oil; and an amount of the shea butter greater than a total of the equal percentages.

3. A method of producing the botanical pain relief ointment of claim 1, comprising:
sequentially mixing the shea butter, the turmeric oil, the myrrh oil, the frankincense oil, the peppermint oil, the olive oil, and the CBD isolate oil in a blender on low speed for about 10 to about 15 minutes.

* * * * *